United States Patent
Alvarez

(10) Patent No.: US 7,291,151 B2
(45) Date of Patent: Nov. 6, 2007

(54) VERTEBRAL FIXATION DEVICE FOR THE TREATMENT OF SPONDYLOLISTHESIS

(75) Inventor: Luis Marquez Alvarez, Reus-Tarragona (ES)

(73) Assignee: Traiber, S.A., Tarragona (ES)

(*) Notice: Subject to any disclaimer, the term of this patent is extended or adjusted under 35 U.S.C. 154(b) by 0 days.

(21) Appl. No.: 10/584,812

(22) PCT Filed: Jul. 25, 2003

(86) PCT No.: PCT/ES03/00338

§ 371 (c)(1),
(2), (4) Date: Jun. 27, 2006

(87) PCT Pub. No.: WO2005/016161

PCT Pub. Date: Feb. 24, 2005

(65) Prior Publication Data

US 2006/0293659 A1 Dec. 28, 2006

(51) Int. Cl.
*A61B 17/56* (2006.01)
(52) U.S. Cl. ....................................................... 606/61
(58) Field of Classification Search .................. 606/61
See application file for complete search history.

(56) References Cited

U.S. PATENT DOCUMENTS

| | | | |
|---|---|---|---|
| 5,782,833 A * | 7/1998 | Haider | 606/61 |
| 5,882,350 A * | 3/1999 | Ralph et al. | 606/61 |
| 6,063,090 A * | 5/2000 | Schlapfer | 606/61 |
| RE37,665 E * | 4/2002 | Ralph et al. | 606/61 |
| 6,371,957 B1 * | 4/2002 | Amrein et al. | 606/61 |
| 6,723,100 B2 * | 4/2004 | Biedermann et al. | 606/73 |
| 6,835,196 B2 * | 12/2004 | Biedermann et al. | 606/61 |
| 2002/0143341 A1 * | 10/2002 | Biedermann et al. | 606/73 |

FOREIGN PATENT DOCUMENTS

| EP | 1 210 914 B1 | 5/2005 |
|---|---|---|
| MX | 9910355 A | 4/2000 |

* cited by examiner

*Primary Examiner*—Eduardo C. Robert
*Assistant Examiner*—Michael J. Araj
(74) *Attorney, Agent, or Firm*—Knobbe Martens Olson & Bear LLP

(57) ABSTRACT

The invention relates to a vertebral fixation device for the treatment of spinal conditions and more specifically spondylolisthesis. The inventive device comprises a screw (1) which is intended to be fixed to a bone and a tulip element (2) comprising vertical notches (3) in which a bar (4) moves vertically, the bar forming the connection between screws (1) belonging to other devices. The position of the aforementioned bar (4) is adjusted in relation to the bone using a support nut (15). Moreover, the bar (4) rests on the upper face of the support nut (15), such that the rotation of the nut (15) determines the vertical displacement of the bar (4) in relation to the bone, the bar remaining fixed in position by the closing screw (5). The invention further comprises a rosette element (8) having an inner housing which is used to house the head of the screw (1) in such a way that the head, and consequently the screw (1), remain connected to the tulip (2).

8 Claims, 5 Drawing Sheets

A-A

VERTEBRAL FIXATION DEVICE FOR THE TREATMENT OF SPONDYLOLISTHESIS

OBJECT OF THE INVENTION

This invention refers to a vertebral fixation device belonging to the area of bone surgery especially designed for the treatment of spinal conditions and more specifically spondylolisthesis.

The object of the invention is that, after implanting a screw in the vertebra, the most suitable tulip element associated with that screw is selected according to the height or displacement of the vertebra. Tulips have a polyaxial orientation that allows distance adjustment and fixing of a bar with respect to the vertebra that acts as a connecting bridge between the other fixings associated with other vertebrae. This tulip allows the fixing of the bar by the lower part forming a block so that neither the bar nor the vertebra can move.

BACKGROUND TO THE INVENTION

Spondylolisthesis consists of the slipping of one vertebra over another either forwards (anterolistesis) or backwards (retrolisthesis) which in any case determines that a vertebra is misaligned with the rest, causing pain and nerve compression.

If the decision is taken to operate to correct this condition, normally screws are fixed to various vertebrae and connected by means of a bar which is subjected to traction to fix or to try to correct the misalignment between vertebrae.

Patent application PCT/ES00/00310 belonging to the applicant for this invention proposes a system for intervertebral fixation for spine treatments, the purpose of which is to allow the implanting of a system of tulips that are physically independent of the rest of the pieces involved in it, allowing the implantation to be made in optimal conditions from the point of view of manipulation as well as from the visual point of view.

The invention fundamentally comprises a screw with a spherical head, a tulip element that can receive the head of the screw, a lower boss which is fixed to the screw and that has a housing on which the bar rests, with the bar protruding through recesses in the tulip, the bar being conveniently fixed by means of another upper boss on which a threaded cap is located that allows for the definitive fixing of the assembly is located. There is a cavity in the spherical head of the screw into which an Allen key can be inserted to facilitate the implanting of the screw in the bone before the rest of the device mechanisms are implanted.

When it is necessary to cope with level differences between vertebrae, normally three systems of screws of different lengths associated with the bar are used; however, it may occur that once a screw length has been chosen, it may require another length and if the screw is changed, it must be for one of a larger diameter, which is sometimes not possible since it does not fit in, resulting in an awkward undertaking during the operation. Another system consists of using tulips that are longer than necessary and that must be cut once they have been installed, which causes another inconvenience during the operation; finally, there are those who advise the bending of the bar in situ, a very laborious undertaking when carried out during the operation, during which the operating time is very important.

DESCRIPTION OF THE INVENTION

The vertebral fixation device that forms the subject of this invention offers the possibility of optimising the above systems used for fixing on the vertebrae and treating spondylolisthesis.

In this sense, the possibility is proposed of using any screw length chosen according to requirements and conveniently fixing it on the bone firstly, then choosing the tulip that appears the most suitable and fixing it to the head of the screw with a simple pressure until it clicks into place. If the tulip is not suitable, a special tool can be used to remove it. Because the tulip has a polyaxial orientation, it allows direction and angle adjustment in order to correctly engage with the bar, which is conveniently fixed above and below, thus solving the above described problem, adding the fact that the entire system is converted into a block, preventing any later movement of the vertebra.

Conventionally, the screw has a spherical head which contains a cavity for inserting the tool that allows its rotation and the subsequent implantation of the screw in the vertebra. There is a rosette element associated with the head, essentially spherical in shape, with axial slots that end in an upper conical protuberance; this rosette is designed to clamp the head of the screw in order to join it to an internal spherical cavity within a tulip, providing it with polyaxial movement while it is not held by the tightening screw.

A threaded section extends above this spherical cavity inside the tulip in which a tightening screw is fitted that acts on the protuberance of the rosette to fix the position of the rosette in that spherical cavity.

In order to remove the screw from the tulip, the tightening screw must first be loosened and then the appropriate tool inserted through the transverse drillings in the tulip that are aligned with the position of the upper conical protuberance. As the tools enter, they act on the conical protuberance, lifting the rosette so that the pressure the rosette exerts on the head of the screw is reduced, releasing it and thus allowing the screw to be removed.

The operation described above could also be carried out if, after tightening the tulip with the screw, they had become locked in an unsuitable direction; it is then necessary to loosen the tightening screw in the rosette in order to free them and thus be able to recover the polyaxial orientation, adjusting the tulip to the desired angle.

The tulip has an exterior threaded section on its lower part designed for the threading of an exterior support nut that constitutes the contact surface on which the bar rests, going at the same time through vertical notches located opposite each other in the upper part of the tulip.

Inside the tulip, there is a threaded section into which a closing screw fits which may extend beyond the tulip, that is, it has an open shape designed to allow the tulip to protrude above and whose lower face presses on the bar. The height of the bar or the distance with respect to the bone is controlled by adjusting the nut on which the bar rests until the required height is achieved, then fixing the position of the bar by tightening the closing screw on the bar.

On the outside of the closing screw there is an essentially cylindrical locking cap on the upper face of which fins are oriented axially and fit into an indentation on the closing screw in such a way that the closing screw rotation determines the screw-cap combined movement in the vertical direction, the locking cap having opposite-facing curved openings in its side wall which fit onto the bar.

To facilitate the rotation of the closing screw, it has a cavity on its upper face of suitable shape and size for inserting the appropriate tool.

DESCRIPTION OF THE DRAWINGS

To complete this description and in order to help the better understanding of the features of the invention, according to a preferential example of its practical embodiment, this description is accompanied by a set of drawings as an integral part thereof where, in an illustrative but not limitative way, the following has been represented.

PREFERENTIAL EMBODIMENT OF THE INVENTION

Figure 1:
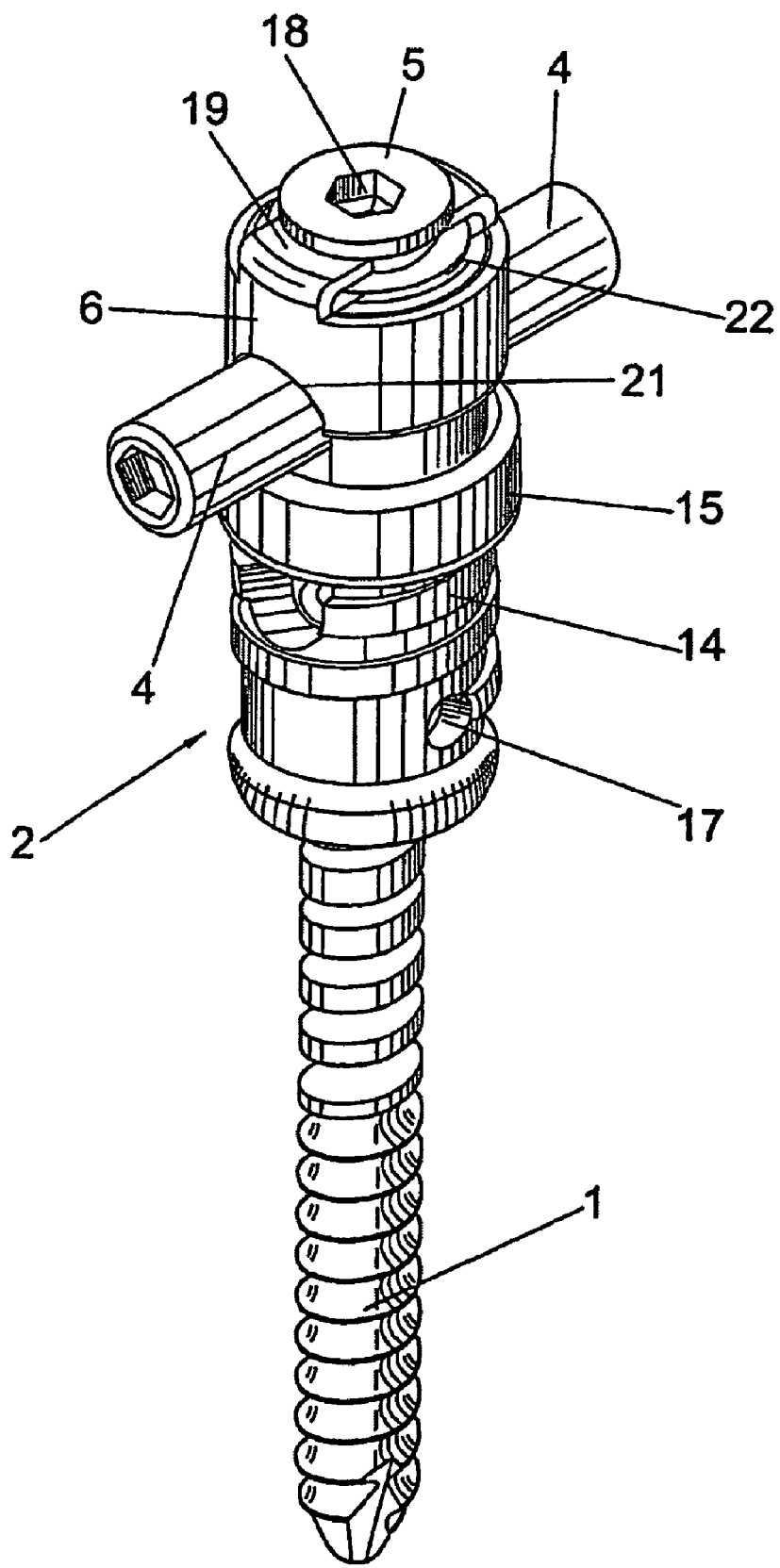
FIG. 1 shows a perspective view of the vertebral fixation device for spondylolisthesis treatment.
Figure 2:
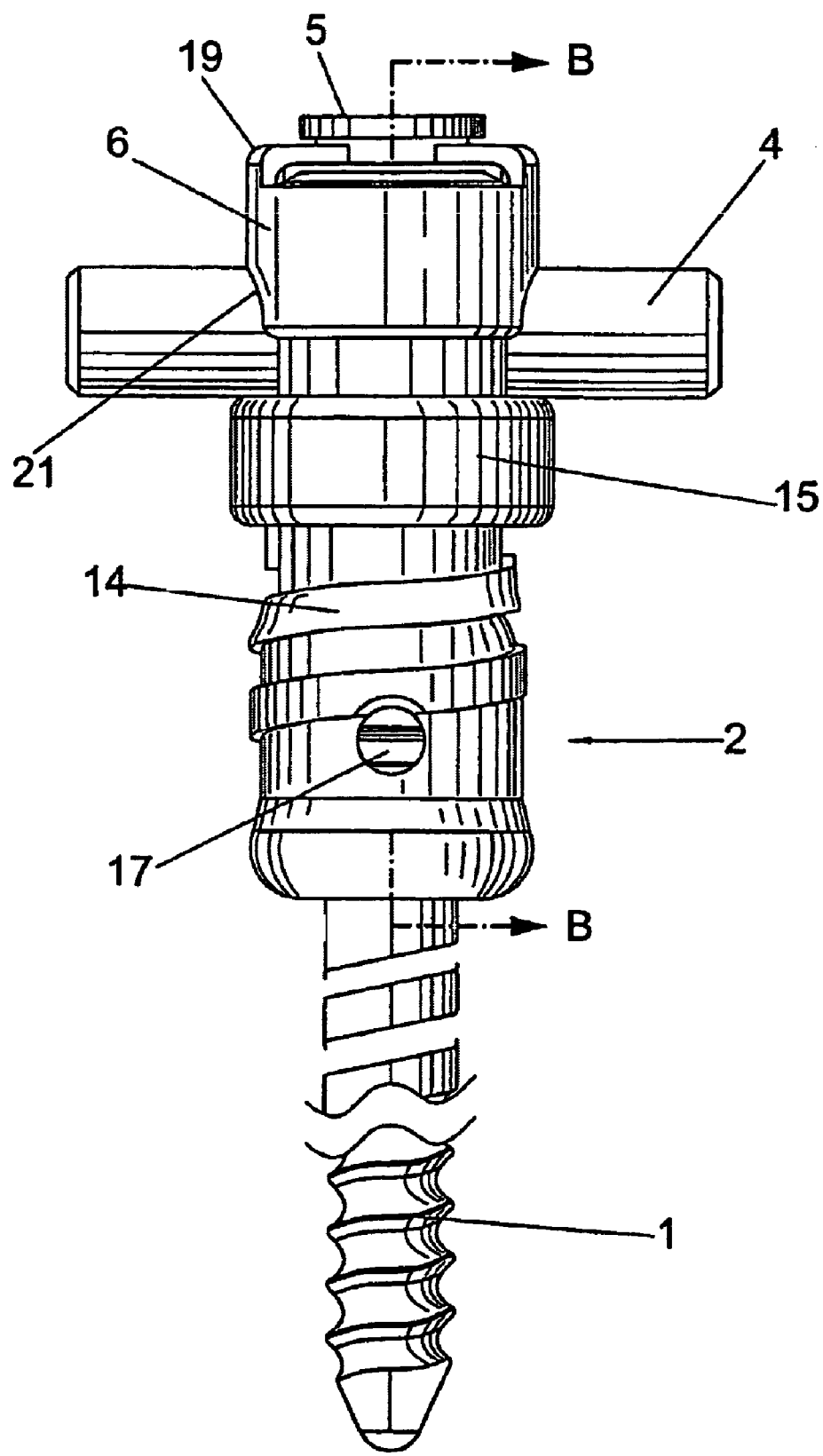
FIG. 2 shows an elevation view of the device that forms the object of this invention.
Figure 3:
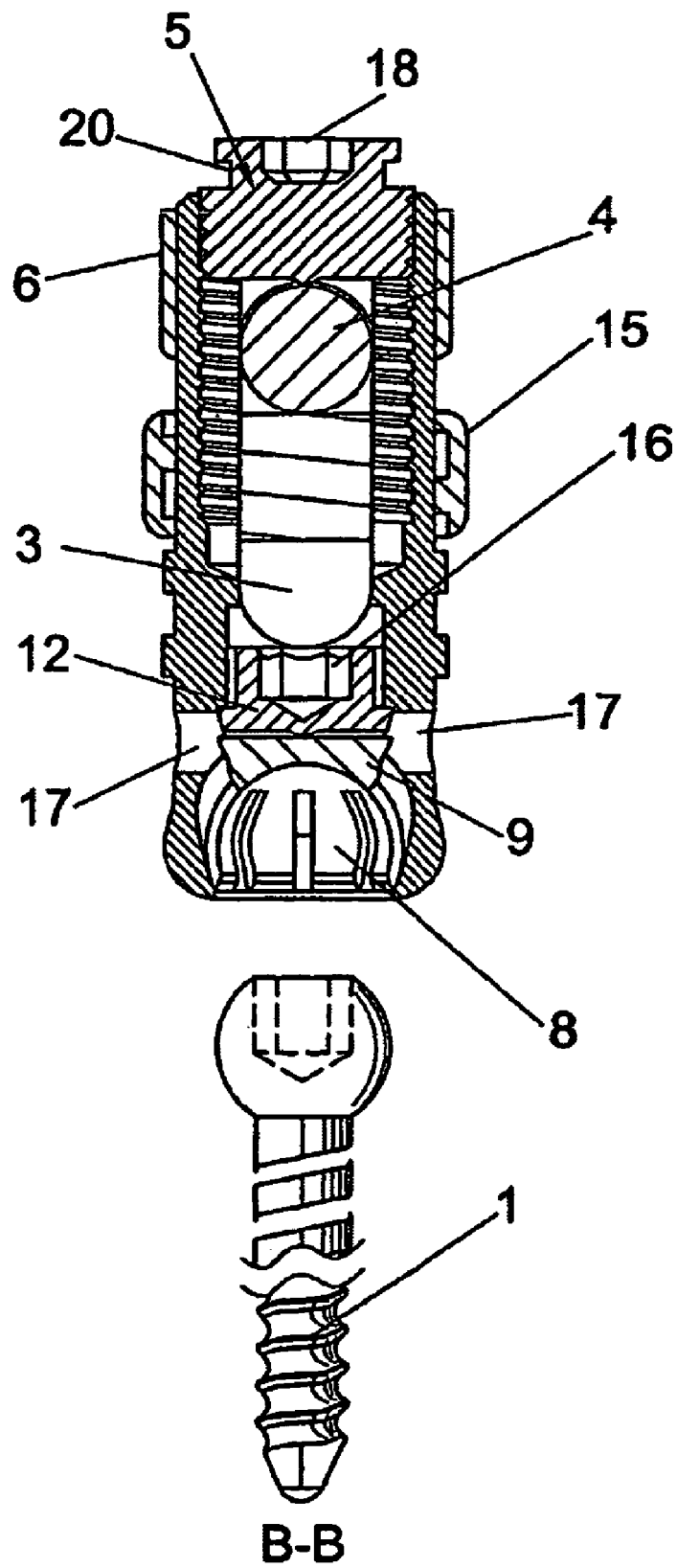
FIG. 3 shows a cross section along B-B in the previous figure.
Figure 4:
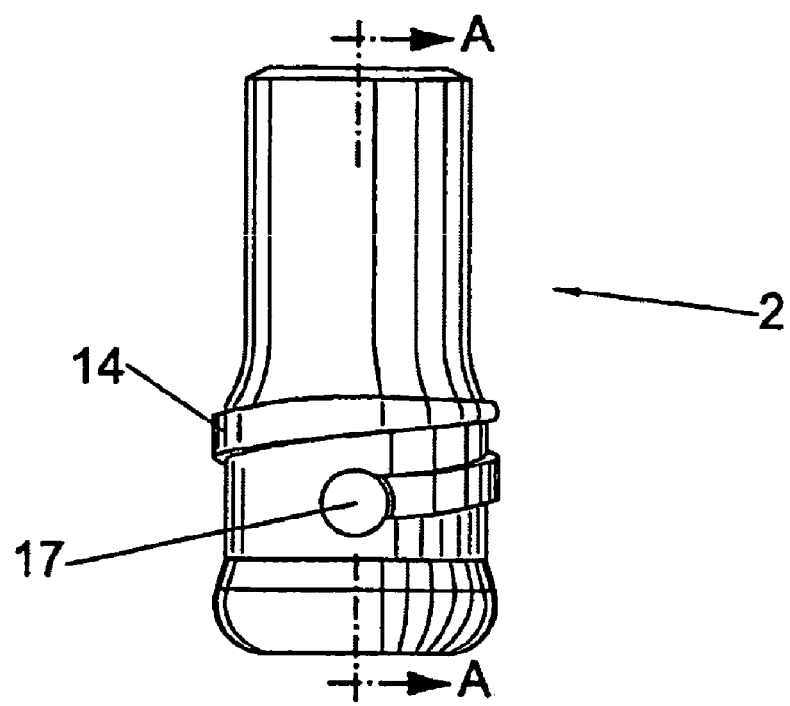
FIG. 4 shows an elevation view of the tulip belonging to the device in the invention.
Figure 5:
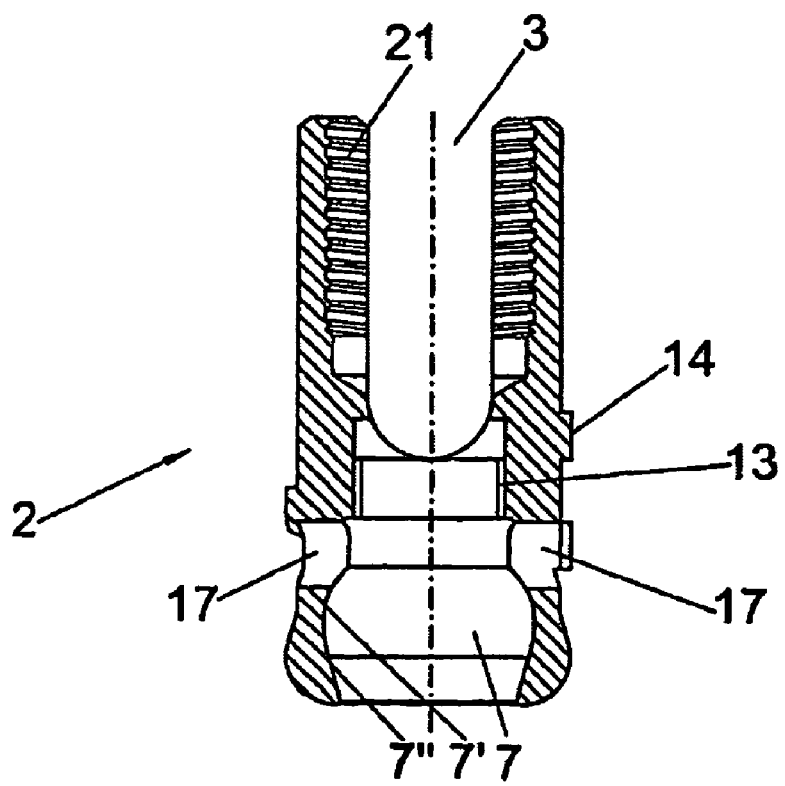
FIG. 5 shows a cross section along A-A in the previous figure.
Figure 6:
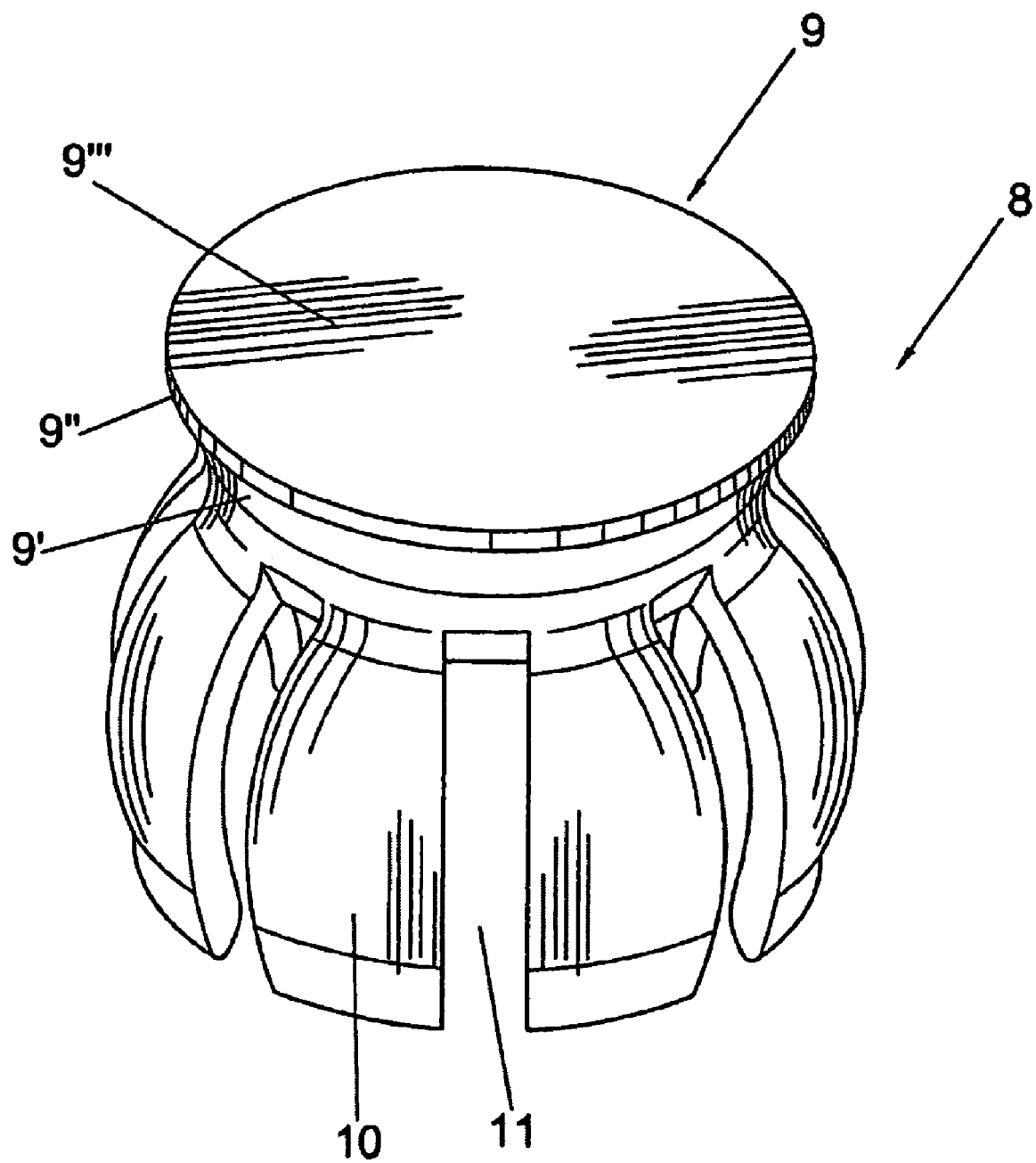
FIG. 6 shows a perspective view of the rosette.

The vertebral fixation device for treating spondylolisthesis that forms the object of this invention starts with the basic incorporation of a screw (1) with a spherical head designed for fixing to a bone, a tulip element (2) that includes: opposite-facing vertical notches (3) on which there is a bar (4) that forms the link between screws (1) of other devices, and an interior threaded section (21) in which a closing screw (5) fits in and rests against the bar (4) and which in its movement drags a locking cap (6).

On the basis of this basic construct, the fixation device is noteworthy because the tulip (2) has a cavity (7) inside and below, delimited by an upper spherical wall (7') and a lower conical wall (7") in which a rosette (8) is located, formed by an upper protuberance (9) that has a conical section (9') ending at the top with another cylindrical section (9") that serves as a movement guide inside the tulip and has a series of flexible slats (10) on its smooth or slightly roughened upper face (9''') which extend down from this upper protuberance (9), separated by slots (11) that form a housing in which the head of the screw (1) is housed and which has free polyaxial orientation and movement, such that a threaded sector (13) located after the cavity (7) moves a tightening screw (12) that acts on the upper face (9''') of the upper protuberance (9) of the rosette (8) in order to close the slats (10) by pressing them against the conical wall (7'), slats (10) which in turn will press and remain fixed on the head of the screw (1).

In order to facilitate the turning of the tightening screw (12), it has an upper cavity (16) that allows the insertion of the corresponding tool.

Likewise, the fixing device is noteworthy because the tulip (2) has on its exterior face a threaded section (14) onto which a support nut (15) is threaded, on the upper face of which the bar (4) rests such that the turning of the support nut (15) determines the movement in height of the bar (4) with respect to the bone to which the screw (1) is screwed, the bar (4) being fixed between the support nut (15) and the closing screw (5) tightened against it (4).

The tulip (2) has two transverse drillings (17) opposite each other aligning with the position of the upper protuberance (9) on the rosette (8) inside the tulip (2) which facilitates the entry of tools to act on the upper protuberance (9) and raise the rosette (8) which is thus disconnected from the head of the screw (1), allowing the latter to be removed.

Equally, the closing screw (5) has a cavity (18) in its upper face into which the appropriate tool is inserted to facilitate its rotation, causing the vertical movement of the locking cap (6) connected to the closing screw (5) by means of folded fins (19) that fit in an indentation (20) on the closing screw (5), with circular holes (21) in the side wall of the locking cap (6) that rest on the bar (4); the movement of the latter being guided in vertical notches (3) in the tulip (2).

The locking cap (6) has recesses (22) defined by the effect of the opposite-facing fins (19) which facilitate the passage of the tulip (2) to allow it to protrude above, while the fins(19) slide inside vertical notches (3) in the tulip (2).

The invention claimed is:

1. Vertebral fixing device for treating spondylolisthesis which has a screw that has a spherical head designed for fixing to a bone, a tulip that incorporates vertical notches aligned with each other in which a bar is placed, forming a link between screws of other devices and an interior threaded section into which fits a closing screw that rests on the bar and moves a locking cap, essentially wherein the tulip has a cavity inside and below, delimited by an upper spherical wall and a lower conical wall in which a rosette is located, formed by an upper protuberance that has a conical section ending at a top with another cylindrical section that serves to guide the movement axially inside the tulip and which on its upper face has a series of flexible slats arranged down from the upper protuberance, separated by slots that form a housing in which the head of the screw is housed and which has free polyaxial orientation movement, there being a threaded section located next to the cavity in which a tightening screw moves, acting on the upper face of the upper protuberance of the rosette to close the slats by pressure on them against the conical wall, slats which in turn will press against the head of the screw to fix it in position.

2. Vertebral fixation device for treating spondylolisthesis according to claim 1 wherein the tulip includes two transverse drillings aligned with the position of the upper protuberance of the rosette inside the tulip which facilitates the insertion of tools to act on the upper protuberance and raise the rosette which is thus disconnected from the head of the screw allowing the latter to be removed.

3. Vertebral fixation device for treating spondylolisthesis according to claim 1 wherein the closing screw has a cavity in its upper face into which a relevant tool is inserted to facilitate the rotation that causes the vertical movement of the locking cap connected to the closing screw by means of folded fins housed in an opening in the closing screw, with circular holes being defined in the side wall of the locking cap that rest on the bar in the guided movement of the latter in the vertical notches in the tulip.

4. Vertebral fixation device for treating spondylolisthesis according to claim 3 wherein the locking cap has recesses defined by the effect of the folding of the fins, that facilitate the passage of the tulip element to allow it to protrude above, while the fins slide inside the vertical notches in the tulip.

5. Vertebral fixing device for treating spondylolisthesis according to claim 3 wherein the fins are housed in vertical notches preventing the opening of the tulip when the pressure is applied to the device with the closing screw in order to tighten the device or devices.

6. Vertebral fixation device for treating spondylolisthesis according to claim 1 wherein the tightening screw has an upper cavity that allows the insertion of a relevant tool to facilitate its rotation.

7. Vertebral fixing device for treating spondylolisthesis according to claim 1 wherein the tulip has polyaxial orientation.

8. Vertebral fixing device for treating spondylolisthesis according to claim 1 wherein the screw, the tulip and the bar, can be suitably tightened together with the screws, tulips and bars of other devices fixed to the vertebrae forming a single block that does not allow the movement of any of the vertebrae.

* * * * *